US008840950B2

(12) United States Patent
Hibbert et al.

(10) Patent No.: US 8,840,950 B2
(45) Date of Patent: Sep. 23, 2014

(54) COMPOSITIONS OF NUTRITION SUPPLEMENTATION FOR NUTRITIONAL DEFICIENCIES AND METHOD OF USE THEREFORE

(76) Inventors: Jacqueline M. Hibbert, Stockbridge, GA (US); Jonathan K. Stiles, Powder springs, GA (US); Kayellen Umeakunne, Pittsburgh, PA (US); Hyacinth I. Hyacinth, Atlanta, GA (US)

( * ) Notice: Subject to any disclaimer, the term of this patent is extended or adjusted under 35 U.S.C. 154(b) by 599 days.

(21) Appl. No.: 13/105,383

(22) Filed: May 11, 2011

(65) Prior Publication Data

US 2011/0294727 A1    Dec. 1, 2011

Related U.S. Application Data

(60) Provisional application No. 61/348,430, filed on May 26, 2010.

(51) Int. Cl.
*A23L 1/29* (2006.01)

(52) U.S. Cl.
USPC ........... 426/648; 426/656; 426/601; 426/658; 514/1.1

(58) Field of Classification Search
USPC .................................. 426/648, 656, 601, 658
IPC ........... A23L 1/29,1/09, 1/305, 1/3053, 1/3055, A23L 1/3056, 1/3006
See application file for complete search history.

(56) References Cited

U.S. PATENT DOCUMENTS

| | | | |
|---|---|---|---|
| 4,261,980 A | | 4/1981 | Cort |
| 4,376,766 A | | 3/1983 | Collinson-Jones et al. |
| 4,866,052 A | | 9/1989 | Hider et al. |
| 4,904,678 A | | 2/1990 | Chima |
| 4,945,083 A | | 7/1990 | Jansen, Jr. |
| 5,006,559 A | * | 4/1991 | Askanazi et al. ............. 514/561 |
| 5,108,754 A | | 4/1992 | Wilburn |
| 5,179,080 A | * | 1/1993 | Rothkopf ....................... 514/5.5 |
| 5,626,884 A | | 5/1997 | Lockett |
| 5,993,221 A | * | 11/1999 | Bistrian ........................ 434/429 |
| 6,254,871 B1 | | 7/2001 | Ohnishi |
| 6,814,983 B2 | | 11/2004 | Giordano et al. |
| 7,214,709 B2 | | 5/2007 | Kimoto et al. |
| 2008/0027024 A1 | * | 1/2008 | Gahler et al. .................. 514/54 |

FOREIGN PATENT DOCUMENTS

| | | |
|---|---|---|
| CN | 101325882 A | 12/2008 |
| CN | 101478891 A | 7/2009 |
| WO | 2007070611 A2 | 6/2007 |

OTHER PUBLICATIONS

International Search Report, mailed Jan. 12, 2012 (International Application No. PCT/US2011/036810, filed May 17, 2011).
Written Opinion of the International Search Authority, mailed Jan. 12, 2012 (International Application No. PCT/US2011/036810, filed May 17, 2011).
Badaloo A., et al., "Whole body protein turnover and resting metabolic rate in homozygous sickle cell disease", Clinical Science, vol. 77, pp. 93-97 (1989).
Salman, E. K., et al., "Protein and Energy Metabolism in Prepubertal Children with Sickle Cell Anemia", Pediatric Research, vol. 40, pp. 34-40 (1996).
Hibbert, J. M., et al., "Erythropoiesis and Myocardial Energy Requirements Contribute to the Hypermetabolism of Childhood Sickle Cell Anemia", Journal of Pediatric Gastroenterology & Nutrition, vol. 43, pp. 680-687 (2006).
Hibbert, J. M., et al., "Proinflammatory Cytokines and the Hypermetabolism of Children with Sickle Cell Disease", Exp. Biol. Med., vol. 230, pp. 68-74 (2005).
Archer, D.R., et al., "C-Reactive Protein and Interleukin-6 Are Decreased in Transgenic Sickle Cell Mice Fed a High Protein Diet", J. Nutr., vol. 138, pp. 1148-1152 (2008).
Sayavongsa, et al., "Vanillic acid excretion can be used to assess compliance with dietary supplements", e-Journal of Clinical Nutrition and Metabolism, vol. 2, pp. e134-e137 (2007).
Abdulmalik, O., et al., "5-hydroxymethyl-2-furfural modifies intracellular sickle haemoglobin and inhibits sickling of red blood cells", Br. J. Haematol. vol. 128, pp. 552-561 (2005).

* cited by examiner

*Primary Examiner* — David Lukton
(74) *Attorney, Agent, or Firm* — Ping Wang; Andrews Kurth, LLP

(57) ABSTRACT

A nutritional supplement composition for treating nutritional deficiencies caused by a medical condition in subjects is disclosed. The present application further discloses a method of using a nutritional supplements composition for treating a subject with complications resulting from sickle cell anemia. The method comprises administering to a subject an effective amount of the nutritional supplement.

23 Claims, 10 Drawing Sheets

COMPOSITIONS OF NUTRITION SUPPLEMENTATION FOR NUTRITIONAL DEFICIENCIES AND METHOD OF USE THEREFORE

This application claims the priority of Provisional Application No. 61/348,430, filed on May 26, 2010, which is incorporated herein in its entirety.

FIELD

This application generally relates to the field of a nutritional supplement designed to treat targeted nutritional problems caused by a medical condition in subjects; in particular, relates to prevention and treatment of nutritional deficiencies in sickle cell anemia subjects.

BACKGROUND

Sickle cell disease is an inheritable hematological disorder based on a mutation in the β-globin gene of hemoglobin. Upon deoxygenation, this mutated hemoglobin polymerizes and causes a shape change (sickling) of the red blood cell. This change in red blood cells leads to obstruction of blood vessels causing a wide variety of complications such as stroke, pulmonary hypertension, end-organ disease and death.

This deformation damages the membrane of subjects' red blood cells and makes the average life of the red blood cells in the range of 10 to 20 days as opposed to 120 days for normal individuals. As a result, subjects suffer from chronic anemia. These damaged red blood cells have a tendency to adhere to the endothelial cells of the blood vessel, neutrophils and platelets, and thus, obstruct blood flow causing frequent painful episodes called "sickle cell crisis," damaging organs and impairing bone joints.

In addition to the fatal or potentially fatal complications, there are serious nonfatal complications of sickle cell disease such as pain. The severity of the pain may vary, but normally requires some form of medical attention, and hospitalization may be necessary. Chronic inflammation is one of the complications of subjects with sickle cell disease and studies from our laboratory show that both circulating CRP and IL-6 are elevated in steady-state children with sickle cell anemia.

In the U.S. alone, approximately 70,000-100,000 people suffer from sickle cell disease. Sickle cell disease is estimated to affect one of every 1,300 infants in the general population, and one of every 500 of African descent. Currently, there is no cure for sickle cell disease. The disease is chronic and lifelong. Life expectancy is typically shortened.

Previous patents involving methods of treating sickle cell disease have been focused mainly on the effects of the sickled red cells, as the only symptom of the disease. Traditional treatment includes vitamin and mineral supplements directed at normalizing erythropoiesis, increasing HbF production, maintaining hydration of the red cells and whole body and blood transfusions to supply normal, red cells.

For example, U.S. Pat. No. 4,945,083, issued Jul. 31, 1990 to Christian Jansen, Jr. describes a method for treating or preventing macrocytic-megaloblastic anemia with multi-factor vitamin formulations. Other combination therapies for sickle cell anemia (HbSS) with formulations that include vitamins are described in U.S. Pat. No. 5,626,884, issued May 6, 1997 to Lockett, and U.S. Pat. No. 7,214,709, issued May 8, 2007 to Kimoto et al. Both describe formulations including ascorbic acid (vitamin C).

The only cure for this disease is bone marrow transplant, which is not widely available. Currently, the only medication, which seems to have some efficacy, is an oral administration of hydroxyurea. This compound increases the cellular content of fetal hemoglobin (HbF), which does not polymerize at low oxygen concentration like HbS. However, hydroxyurea has some negative side effects, such as bone marrow suppression, and a life-long administration may not be recommended.

Accordingly, there is a need in the art for the treatment of sickle cell disease or the complications associated therewith. The present invention fulfills these needs and further provides other related advantages.

SUMMARY

One aspect of the present invention relates to a method for treating conditions associated with fast energy metabolism or high energy requirement. The method includes administering to a subject in need of such treatment a daily nutritional supplement having total calories of about 700-980 kcal, wherein about 10-20% of the total calories are derived from protein, about 25-40% of the total calories are derived from fat, and about 45-65% of the total calories are derived from carbohydrate.

In one embodiment, the conditions associated with abnormally slow energy metabolism include malnutrition, anorexia, cancers, AIDS and aging.

In another embodiment, the conditions associated with high energy requirement include sickle cell anemia, pregnancy, lactation, growth, exercise, cancers, infectious diseases and recovery from surgical and other injuries.

In a related embodiment, the condition associated with abnormally high energy requirement is sickle cell anemia.

In another embodiment, the nutritional supplement is administered orally in the form of a snack. In a related embodiment, the nutritional supplement is administered orally as the last snack before sleeping. In another related embodiment, the nutritional supplement is administered as snacks after each meal.

Another aspect of the present invention relates to a nutritional supplement to normal diet for treating conditions associated with abnormally slow energy metabolism or high energy requirement. The nutritional supplement contains protein in an amount that provides about 10-20% of the total calories, fat in an amount that provides about 25-40% of the total calories, and carbohydrate that provides about 45-65% of the total calories.

In a related embodiment, the nutritional supplement contains about 14% protein energy (i.e., about 24-34 grams of protein for a 700-980 kcal daily dose), about 32% of fat energy (i.e., about 25-35 grams of fat for a 700-980 kcal daily dose) and about 55% carbohydrate energy (i.e., about 96-135 grams carbohydrates fat for a 700-980 kcal daily dose).

In another embodiment, the nutritional supplement further includes at least one food grade amino acid selected from the group consisting of arginine, histidine, leucine, valine, cysteine and glutamine.

In a related embodiment, the arginine, histidine, leucine, valine, cysteine and glutamine are included in the dose of 8-14 mg/kg body weight/day for adults and 22-44 mg/kg body weight/day for children.

In another embodiment, the nutritional supplement further contains S-ally cysteines, S-allylmercapto cysteine and fructosyl arginine. In a related embodiment, the supplement contains a garlic extract containing S-allyl cysteines, S-allylmercapto cysteine and fractosyl arginine.

In another embodiment, the nutritional supplement further contains one or more antioxidants. Suitable antioxidants for administration with the present composition include, but are not limited to, Vitamin A, Vitamin C, Vitamin E, β-carotene, selenium and other conventional antioxidants.

In a related embodiment, antioxidants are Vitamin C and Vitamin E.

In another embodiment, the nutritional supplement further contains one or more of the following: Vitamin A 8,250-250,000 I.U., Vitamin B-1 25-1000 mg, Vitamin B-2 25-1000 mg, Vitamin B-6 25-1000 mg, Vitamin B-12 25-1000 mcg, Vitamin C 25-1000 mg, Vitamin D 100-4000 I.U., Vitamin E 25-1000 I.U., Niacinamide 25-1000 mg, Para-aminobenzoic acid (PABA) 25-1000 mg, Pantothenic Acid 25-1000 mg, Choline Bitartrate 25-1000 mg, Inositol 25-1000 mg, Rutin 8.25-250 mg, Citrus Bioflavonoid Complex 8.25-250 mg, Betaine Hydrochloride 8.25-250 mg, Hesperidin Complex 1.25-50 mg, Folic Acid 100-4000 mcg, Biotin 25-1000 mcg, Calcium 10-400 mg, Iron 8.25-250 mg, Magnesium 5-100 mg, Zinc 5-100 mg, Potassium 3.75-150 mg, Manganese 1.5-60 mg, Iodine 37.5-1500 mcg, Chromium 3.75-150 mcg, and Selenium 2.5-100 mcg.

In another embodiment, the nutritional supplement further contains one or more of L-lysine-L-phenylalanine, L-lysine-L-tyrosine, L-histidine-L-lysine-L-tyrosine-L-histidine, in particular L-lysine-L-phenylalanine, and salts thereof at a per diem dose within the range of from 10 to 150 mg/kg, preferably from 20 to 80 mg/kg.

In another embodiment, the nutritional supplement further contains thiocyanates in an amount of 100-500 mg. In a related embodiment, the thiocyanate is mixed with Vitamin B6 at a weight ratio of about 20:1.

In another embodiment, the nutritional supplement is a protein/energy dense, low bulk biscuit further containing pharmaceutically acceptable carriers, diluents and/or adjuvants.

Another aspect of the present invention relates to a kit comprising a nutritional supplement to normal diet for treating conditions associated with abnormally slow energy metabolism or high energy requirement, and an instruction on how to use the nutritional supplement. The nutritional supplement contains protein in an amount that provides about 10-20% of the total calories, fat in an amount that provides about 25-40% of the total calories, and carbohydrate that provides about 45-65% of the total calories.

In one embodiment, the nutritional supplement is formulated in a ready-to-dispense form.

In another embodiment, the nutritional supplement is formulated in a ready-to-dispense single-dose form designed for complete consumption as a snack.

In another embodiment, the nutritional supplement is formulated in a ready-to-dispense three-dose form designed as a snack after each meal.

In another embodiment, the nutritional supplement is formulated for complete consumption as a two-pack snack to be taken in the morning and evening.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Cogent evidence has long shown that sickle cell patients have higher than normal metabolic requirements for protein, energy and specific amino acids, particularly those amino acids associated with growth, repair, energy expenditure and more recently, antioxidant and inflammatory status. The present invention provides a supplement of increased energy and protein to address the malnutrition and poor immune status, plus include increased levels of key amino acids required for whole body growth and development, which are low in sickle cell patients because they are diverted toward meeting the increased requirement for synthesis of red cells and inflammatory proteins.

One aspect of the present invention relates to a method for treating conditions associated with abnormally slow energy metabolism or high energy requirement. The method includes administering to a subject in need of such treatment a daily nutritional supplement having total calories of about 700-980 kcal, wherein about 10-20% of the total calories are derived from protein, about 25-40% of the total calories are derived from fat, and about 45-65% of the total calories are derived from carbohydrate.

Conditions associated with abnormally slow energy metabolism include, but are not limited to, under nutrition such as caused by food shortage (famine) and diseases characterized by cechexia, e.g., anorexia, cancers, AIDS, other infectious diseases and aging. Conditions associated with high energy requirements and/or increased nutritional needs include, but are not limited to sickle cell anemia, pregnancy, lactation, growth and recovery from surgical and other injury. The use of the present invention also extends to many other conditions with similar nutritional requirements. In one embodiment, the condition associated with abnormally fast energy metabolism is sickle cell anemia.

Resting energy expenditure is increased in children and adults with sickle cell anemia by 16 to 20% (Badaloo et al., Clinical Science 77: 93-97, 1989; Salman et al., Pediatr Res 40: 34-40, 1996; and Hibbert et al., J Pediatr Gastroenterol Nutr 43: 680-687, 2006).

Resting energy expenditure is approximately 70% of total energy expenditure. An additional 20% of the estimated total energy requirement would be 350 and 490 kcal for children and adults, respectively. The energy supplement provides an additional 40% of the usual energy requirement for each individual (about 700 to 980 kcal per day). This estimation accounts for energy and protein losses during digestion and absorption, i.e. efficiency of utilization, and covers any initial underestimate. Adjustment for the initial estimation can be made following the pilot intervention and during the intervention on an individual basis. It has been demonstrated that a higher than normal protein diet for mice (35% versus 20% of energy from protein respectively) increased rate of weight gain in weanling ss mice and reduced circulating inflammatory proteins C-reactive protein (CRP) and interleukin-6 (IL-6) (Archer et al., J Nutr 138: 1148-1152, 2008). Indeed, chronic inflammation is one of the complications of patients with sickle cell disease and studies show that both circulating CRP and IL-6 are elevated in steady-state children with sickle cell anemia (Hibbert et al., Exptl Biol Med 230: 68-74, 2005). A dietary supplement may alleviate some complications of sickle cell anemia.

In certain embodiments, the supplement is a balanced formula providing the additional energy requirement for each individual as a food supplement with 700-980 kcal energy supplied by 10-20% protein derived energy, 25-40% fat derived energy, and 45-65% carbohydrate derived energy.

In one embodiment, the supplement contains 14% protein derived energy, 32% fat derived energy and 55% carbohydrate derived energy. This would amount to an additional 24-34 grams protein, 96-135 grams carbohydrate and 25-35 grams fat per day, respectively, for the 700-980 kcal that is administered via the supplement.

Suitable protein sources include animal proteins and plant proteins. Non-limiting examples include, but are not limited to, whey protein, soy protein, milk protein, egg protein, casein, peanut flour, nut meats, and combinations thereof. Soy protein is extracted from soybean and is considered to be an economical protein source. The most popular types of soy protein are soy protein isolates and soy protein concentrates. Soy protein isolates are highly digestible and a good source of amino acids and isoflavones. In addition, they are low in fat, calories, and cholesterol. For vegetarians, this is a primary source of protein. Whey protein is derived from whey, which is a by product obtained from making cheese. Functionally, whey proteins are highly soluble even under acidic conditions. There are primarily two forms of whey protein, whey protein isolate and whey protein concentrate. Both are extremely high quality proteins that are highly digestible. However, whey protein isolate is somewhat superior because it is higher in protein and has lower fat, lactose, and flavor levels than whey protein concentrate. Casein is the primary protein found in milk protein, which is about 80% casein and 20% whey protein. Casein includes caseinates, which are available in three main types, sodium, calcium, and potassium. Spray dried egg whites are used in some "egg and milk" protein powder mixes.

Suitable fat sources include, but are not limited to, chocolate, peanut butter, fat substitutes, vegetable fats, tropical fats, animal fats, dairy/milk and combinations thereof.

Suitable carbohydrate sources include, but are not limited to, starch, sugar, gels, syrups, honey, molasses, rice syrups, and combinations thereof.

In another embodiment, the supplement further contains S-allyl cysteines, S-allylmercapto cysteine and -fructosyl arginine. In a related embodiment, the supplement contains a garlic extract containing S-allyl cysteines, S-allylmercapto cysteine and fructosyl arginine.

In another embodiment, the supplement further contains one or more antioxidants. Suitable antioxidants for administration with the present composition include, but are not limited to, Vitamin A, Vitamin C, Vitamin E, β-carotene, selenium and other conventional antioxidants. Preferred among the antioxidants are Vitamin C and Vitamin E. In a related embodiment, antioxidants are Vitamin C and Vitamin E.

In another embodiment, the nutritional supplement further contains one or more of the following: Vitamin A 8,250-250,000 I.U., Vitamin B-1 25-1000 mg, Vitamin B-2 25-1000 mg, Vitamin B-6 25-1000 mg, Vitamin. B-12 25-1000 mcg, Vitamin C 25-1000 mg, Vitamin D 100-4000 I.U., Vitamin B 25-1000 I.U., Niacinamide 25-1000 mg, Para-aminobenzoic acid (PABA) 25-1000 mg, Pantothenic Acid 2.5-1000 mg, Choline Bitartrate 25-1000 mg, Inositol 25-1000 mg, Rutin 8.25-250 mg, Citrus Bioflavonoid Complex 8.25-250 mg, Betaine Hydrochloride 8.25-250 mg, Hesperidin Complex 1.25-50 mg, Folic Acid 100-4000 mcg, Biotin 25-1000 mcg, Calcium 10-400 mg, Iron 8.25-250 mg, Magnesium 5-100 mg, Zinc 5-100 mg, Potassium 3.75-150 mg, Manganese 1.5-60 mg, Iodine 37.5-1.500 mcg, Chromium 3.75-150 mcg, and Selenium 2.5-100 mcg.

Amino acids L-arginine, histidine, leucine, valine, cysteine and glutamine known to be in greater demand for sickle cell anemia patients, is added to the supplement at the requirement for normal healthy children 1.0 to 12 years (22-44 mg/kg/d.) and for adults (8-14 mg/kg/d), i.e. a 50 kg person would receive 6 amino acids a 7 8 mg/kg each for a total of 2.4 grams of supplemental amino acid/day. The added amino acids are food grade, purchased from Ajinomoto Aminoscience LLC (Raleigh, N.C.).

Vanillin food flavor is added to the supplement and urinary vanillic acid, the major excretory metabolite of vanillin, is measured as a biochemical marker of compliance with supplement consumption (Sayavongsa et al., e-J Clin Nutr Metabolism 2: e134-e137, 2007), in addition to traditional compliance monitoring.

In one embodiment, the supplement of the present invention is given to children and adults with a confirmed diagnosis of sickle cell anemia, who are underweight (having a body mass index of 17 or less for children and 20 or less for adults) and who have not been treated with frequent blood transfusions or hydroxyurea. The supplement is given as a nutritional supplement to the normal diet, consumed daily as the last snack prior to bedtime. It supplies an additional 40% of energy (calories) to the normal daily individual energy consumption.

Administration

The supplement is in the form of a protein/energy dense, low bulk cookie. In one embodiment, the nutrition supplement is administered orally as a snack or snacks. The required daily amount (700-980 kcal per day) may be administered in single dose as the last snack before sleeping, or in two or more doses during the day (e.g., morning and afternoon, or after each meal).

If the formula is designed for complete consumption as the last snack before sleeping, it is imperative that it should supply extra calories and protein without bulk. The supplement formulation may be adapted for alternative methods of administration. Examples (include, but are not limited to): liquid formulations (milk shake, energy drink, infusions), candy bar, cookies, etc.

KITS

The invention also encompasses a kit comprising a nutritional supplement to normal diet for treating conditions associated with abnormally slow energy metabolism or high energy requirement, and an instruction on how to use the nutritional supplement. The nutritional supplement contains protein in an amount that provides about 10-20% of the total calories, fat in an amount that provides about 25-40% of the total calories, and carbohydrate that provides about 45-65% of the total calories. In one embodiment, the nutritional supplement is formulated in a ready-to-dispense form.

The present invention is further illustrated by the following examples that should not be construed as limiting. The contents of all references, patents, and published patent applications cited throughout this application, as well as the Figures and Tables, are incorporated herein by reference.

EXAMPLE 1

Nutritional Supplement Study

Twelve children (SS) with sickle cell anemia (SCA)) at ages between 6-12 were randomly allocated into the placebo (5) group and supplement (7) group, and were given either a placebo cookie (for placebo group) or the supplement cookie (for supplement group). Normal children without SCA, but similar age served as controls (AA, n=9). Information on anthropometric, body composition, resting energy expenditure, blood levels of amino acids, and production of reactive oxygen species and level of consumption of natural antioxidants were collected. Data analysis was done on an intent-to-treat basis (gold standard), meaning that irrespective of how far each participant went in the study, all participants were included in the analysis of their allocated group. The numbers of participants (n) during the study are as follows:

Baseline; n=9 for AA, n=5 for placebo and 7 for supplement SCA groups

SCA Intervention Periods 2 weeks; n=5 for placebo and 3 for supplement
1 month; n=5 for placebo and 3 for supplement
2 month; n=4 for placebo and 3 for supplement
3 month; n=2 for placebo and 3 for supplement
4 month; n=3 for placebo and 2 for supplement.

Figure 1:
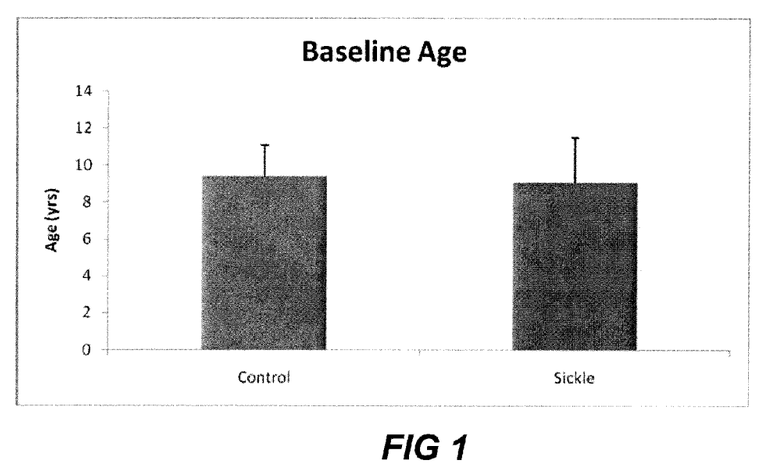
FIG. 1 is a diagram showing that the average age was not different for the control children versus those with sickle cell anemia.
Figure 2:
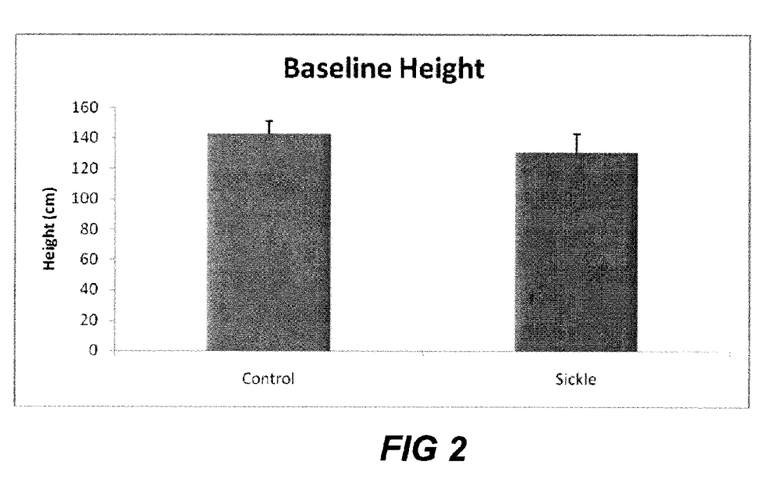
FIG. 2 is a diagram showing that the average height was not different for the control children versus those with sickle cell anemia.
Figure 3:
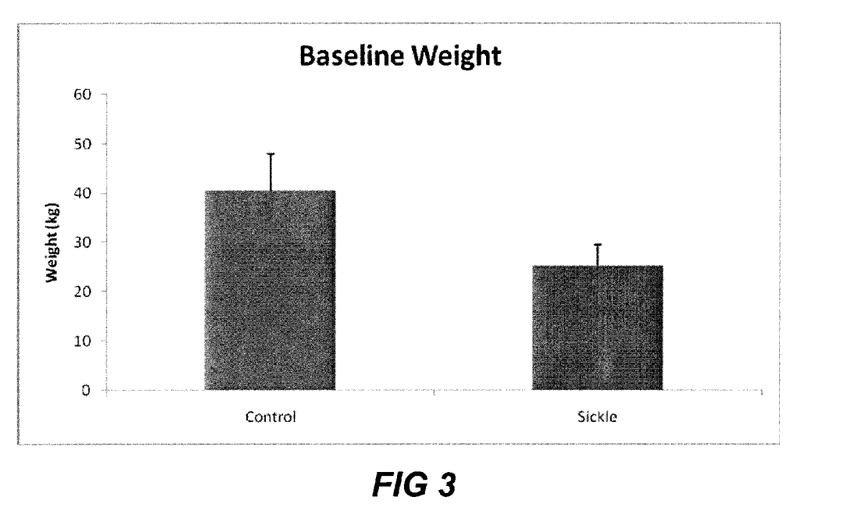
FIG. 3 is a diagram showing that children with sickle cell anemia have significantly lower weight compared with age matched healthy controls.
Figure 4:
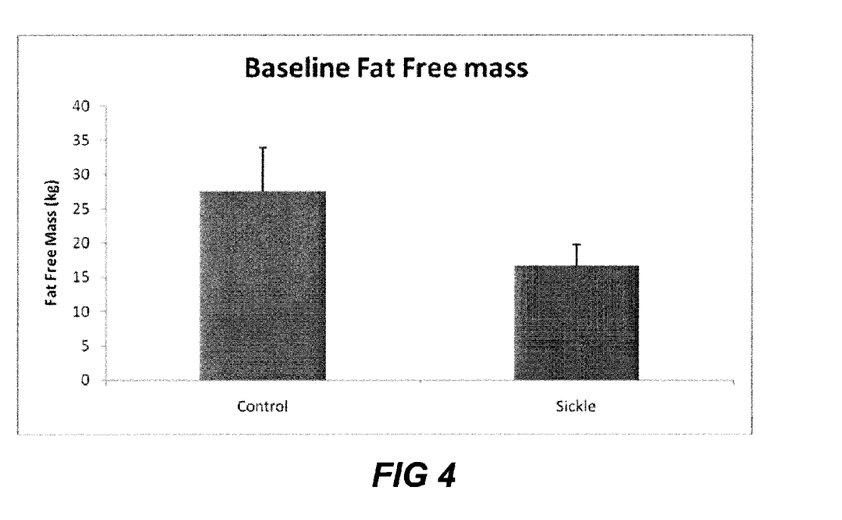
FIG. 4 is a diagram showing that sickle cell children had significantly lower fat free mass compared with controls.
Figure 5:
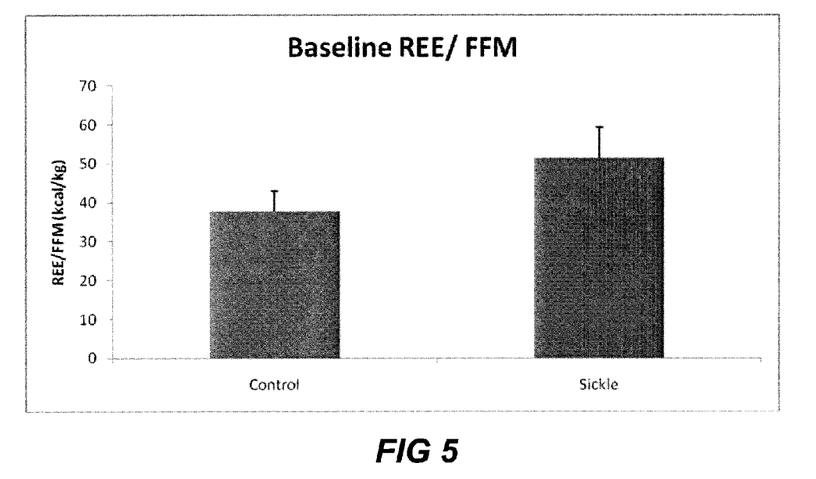
FIG. 5 is a diagram showing that sickle cell children had significantly higher resting energy expenditure (REE) for amount of fat free mass compared with controls.

At baseline the AA and SCA groups were similar in Age (9.4 vs. 9.1, FIG. 1), with moderate difference in height (143 cm vs. 130.6 cm, FIG. 2) but their weight was markedly different (40.5 kg vs. 25.2 kg, FIG. 3) and thus their body mass index (BMI) (20 vs. 14.7), indicating a subnormal nutritional status for age. The children with sickle cell anemia also showed a lower fat free mass (FFM) or lean body mass (16.7 kg vs. 27.6 kg, FIG. 4), but a higher resting energy expenditure (REE) for the amount of FFM as indicated by a higher REE to FFM ratio (FIG. 5). The children with sickle cell anemia were then given either placebo or supplement cookie for 3-4 months and the results collected are summarized below:

Anthropometry, Body Composition and Oxidant Stress Level

Figure 6:
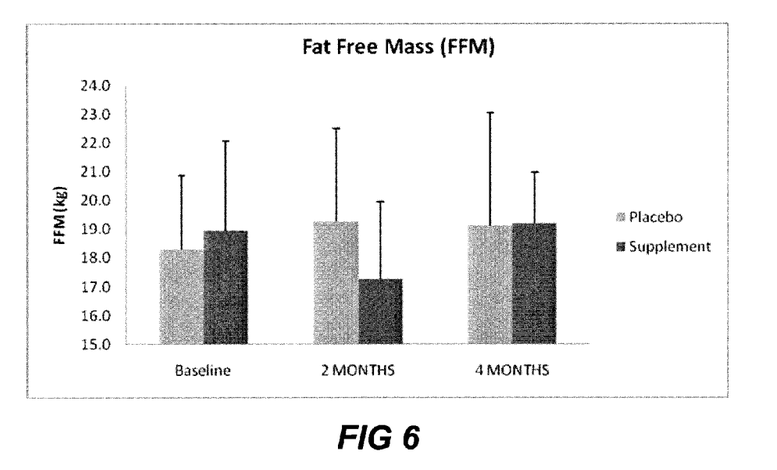
FIG. 6 is a diagram showing that FFM increased by 11.0% from 2 to 4 months for the supplemented group versus a slight decrease (1.0%) for the placebo group. The fluctuations in the number of participants may have contributed to the changes observed between baseline and 2 month.

There was no change in BMI for either the placebo or supplement group from baseline to 4 months. As shown in FIG. 6, the fat free mass (FFM) increased by 4.4% for placebo and decreased by 0.3% for the supplement groups when comparing the baselines with 4 months measurements. But further analysis from 2 months to 4 months showed an 11% increase for the supplement group as opposed to only 0.8% for the placebo group.

Figure 7:
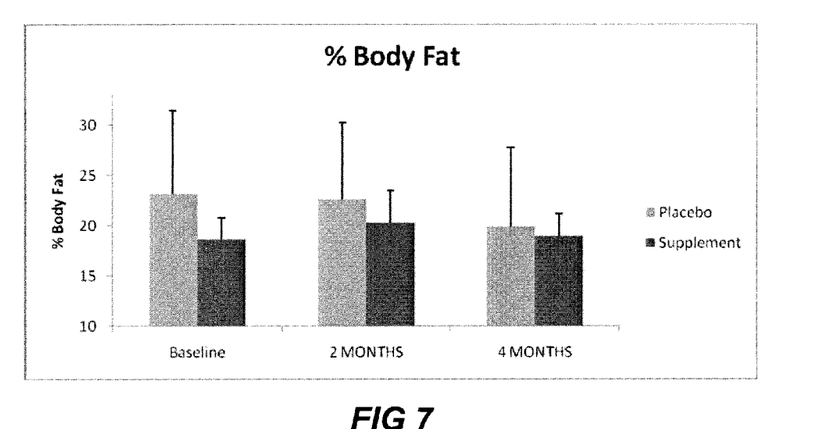
FIG. 7 is a diagram showing that percentage body fat was lower at baseline for the supplemented vs. placebo group, and did not change significantly over time; indicating that there was no accumulation of fat calories due to increased calorie consumption from the supplement.

As shown in FIG. 7, the % body fat for the children with SCA on supplement was lower than that for those on placebo. The graph showed that it was lower (17.3% vs. 23.1%) at baseline and stayed so even after 4 months on the supplement; indicating that the additional nutrient and energy provided is being used up and not allowed to accumulate and create unnecessary and/or unhealthy weight gain. During this feeding period, there was a 0.3% gain in weight from baseline among the supplement group as opposed to a 0.5% decrease in weight for the placebo group.

Figure 8:
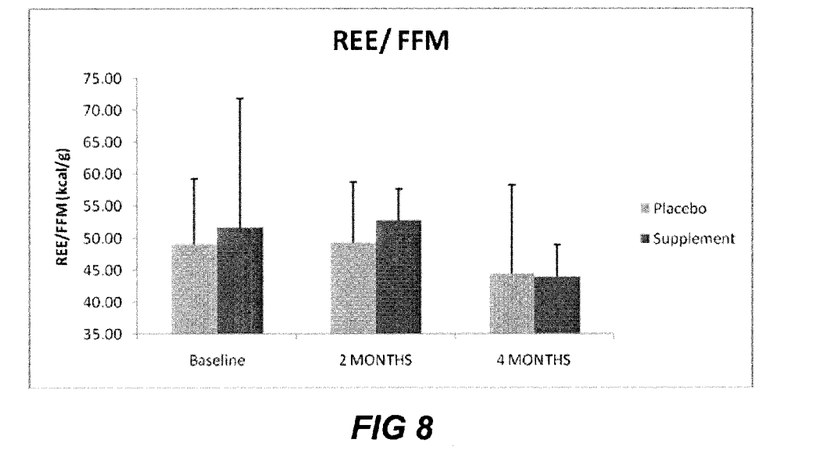
FIG. 8 is a diagram showing that the supplemented group showed a larger decrease (15.1% vs 9.5%) in resting energy expenditure normalized for fat free mass (REE/FFM ratio) compared with placebo. This result represents an increase in FFM, but also a decrease in gross REE value.

The average resting energy expenditure (REE) for the children on supplement was higher (977.7 cal vs. 898 cal) than of those on placebo at baseline. By 4 months, the resting energy expenditure has decreased by 14.2% for the supplement group compared with 5.5% for those on placebo. FIG. 8 shows a 15.5% decrease in the ratio of REE to FFM for the supplement group compared with 9.5% for the group on placebo. Note that under normal circumstance, FFM is one of the major determinants of REE. In this case despite the fact that there was no increase in REE (probably because it was already too high for the amount of FFM at the baseline) the increase in the FFM earlier noted meant a decrease in the REE to FFM ratio towards normal for the amount of FFM.

There was also a decrease (42.4% vs. 35.7%) in the level oxidant stress from baseline for the supplement group compared with the placebo group. Oxidant stress here measured as the concentration of reactive oxygen species (dROMS).

Plasma Amino Acids Levels

The plasma levels of some of the amino acids measured also improved for the supplement group more than the placebo. These amino acids are those we supplemented and are known to be significantly lower in SCA patients, as indicated by the baseline values (except cysteine and cystine) when one compares both placebo and supplement values to the controls (AA).

Figure 9:
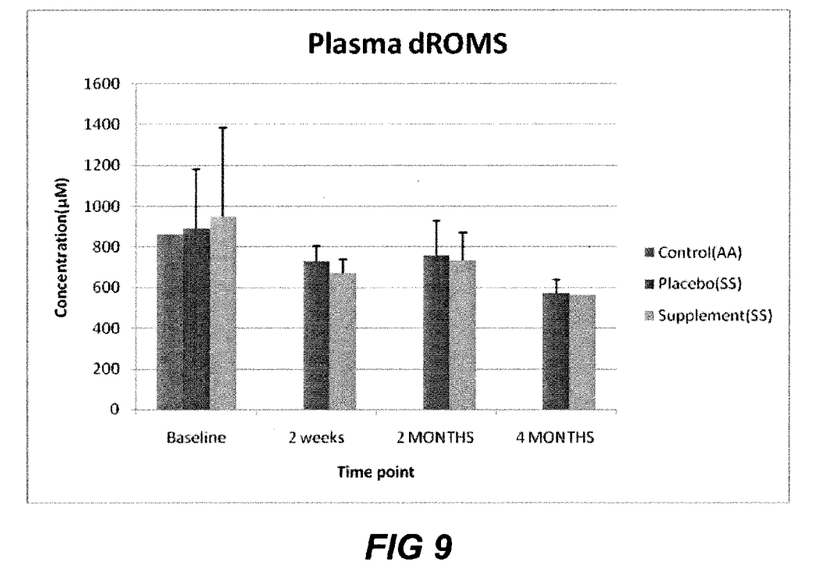
FIG. 9 is a diagram showing that the supplemented group showed a 42.4% decrease in dROM, an index of oxidative stress, compared with a 35.7% for the placebo group.
Figure 10:
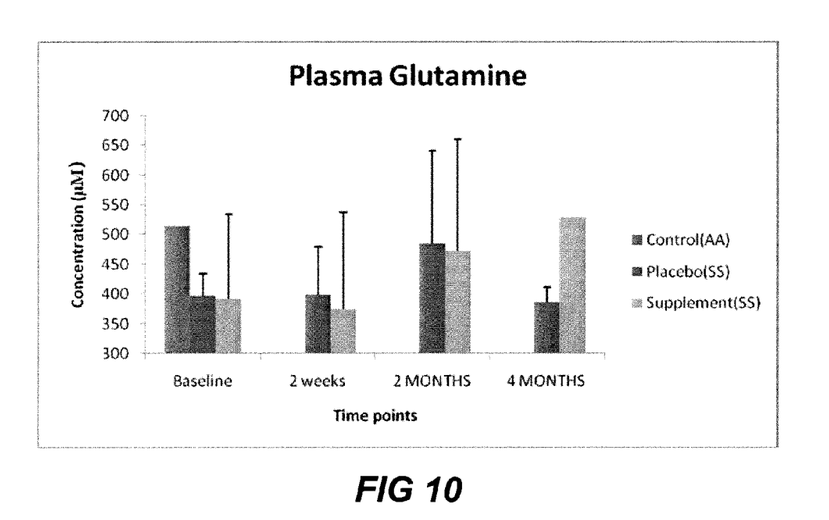
FIG. 10 is a diagram showing a 34.9% increase in plasma glutamine level for the supplemented group vs. a net decrease of 2.9% for the placebo group. Glutamine is useful as a neurotransmitter and a source of energy for the intestinal cells. It also has been shown to reduce REE in sickle cell children.
Figure 11:
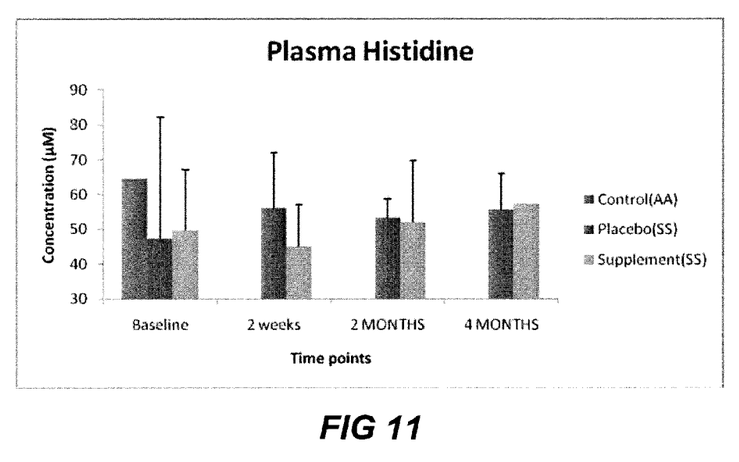
FIG. 11 is a diagram showing that circulating histidine levels increased by 15.2% for the supplemented vs. 17.8 for the placebo group, suggesting no group difference. Histidine is an essential amino acid needed for growth and repair.
Figure 12:
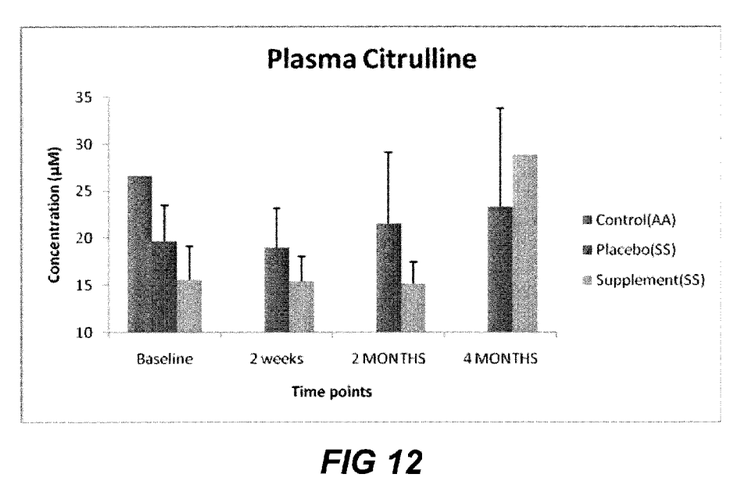
FIG. 12 is a diagram showing that plasma citrulline levels increased by 84.7% for supplemented vs. 18.6% for the placebo groups. Citrulline is essential for vascular and muscle strengthening functions and is an intermediate of the urea cycle pathway.
Figure 13:
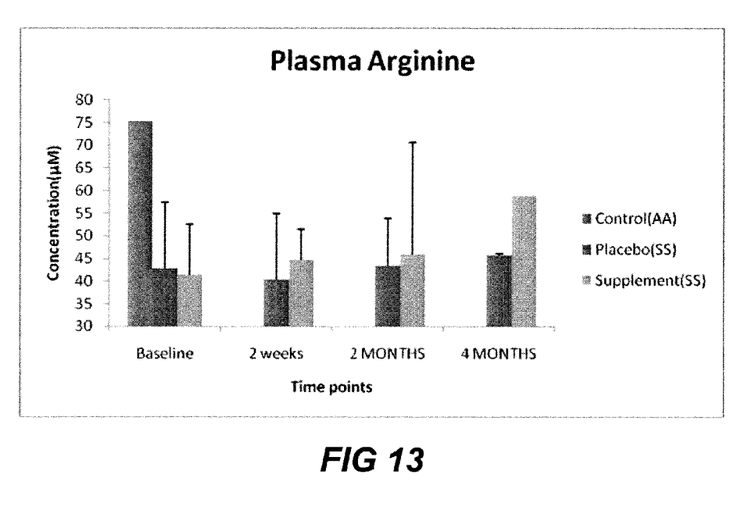
FIG. 13 is a diagram showing that plasma arginine levels increased by 42.7% for the supplemented vs. 6.9% for placebo groups. Like citrulline, arginine is needed to generate nitric oxide (NO) needed for maintaining normal vessel tone among other essential functions and is a product in the urea cycle pathway.
Figure 14:
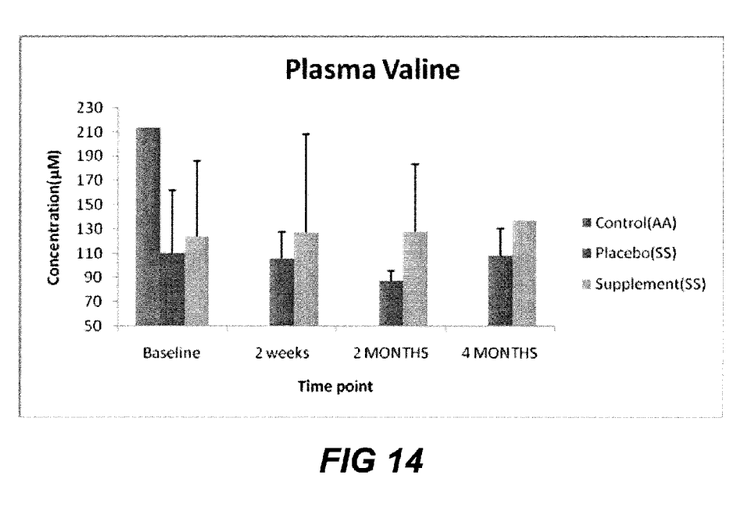
FIG. 14 is a diagram showing that plasma valine levels increased by 11.2% for the supplemented group, vs. a 2.2% reduction for the placebo group. Valine is required for normal muscle and energy metabolism, immune function and reducing muscle inflammation. It is one of the branched chain essential amino acids.
Figure 15:
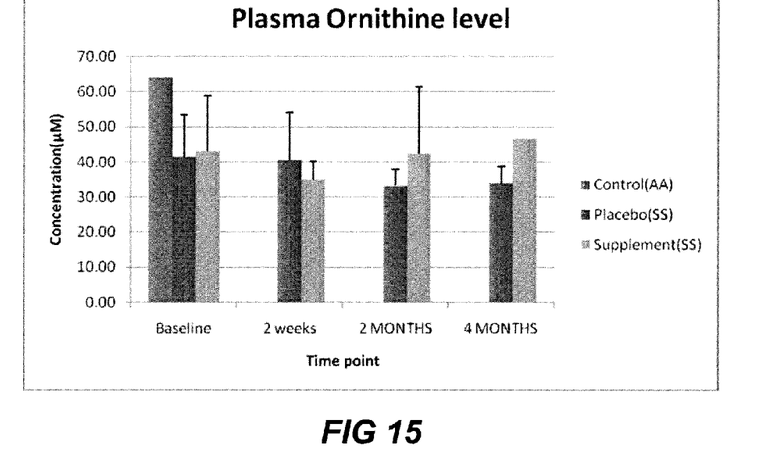
FIG. 15 is a diagram showing that plasma ornithine levels were increased by 8.4% for the supplemented group vs. a decrease of 17.9 for the placebo group. Ornithine is an essential intermediate in the urea cycle and is one of the products of hydrolysis of arginine (by arginase) to urea.
Figure 16:
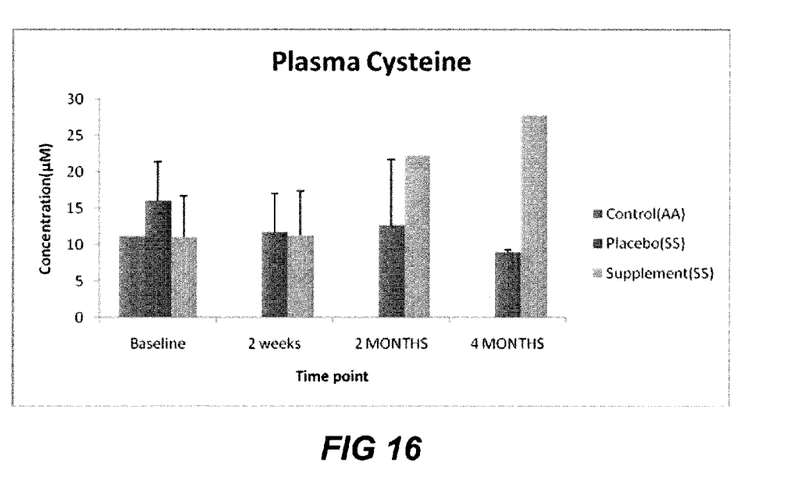
FIG. 16 is a diagram showing that the supplemented group showed a 152% increase in cysteine levels vs. a 43.8% decrease for the placebo group. Cysteine is essential for the synthesis of cystine, glutathione, and many metaloprotein enzymes and transport molecules.
Figure 17:
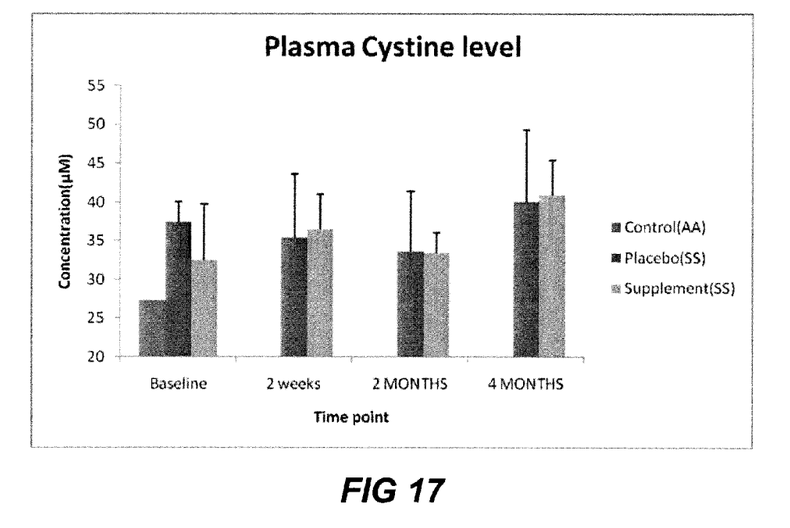
FIG. 17 is a diagram showing that plasma cystine increased for both groups, for the supplemented group cystine increased 26% vs. 8% for the placebo group. Cystine is an amino acid needed for the synthesis of structural proteins such as hair. Its level tends to mirror the levels of its precursor cysteine.
Figure 18:
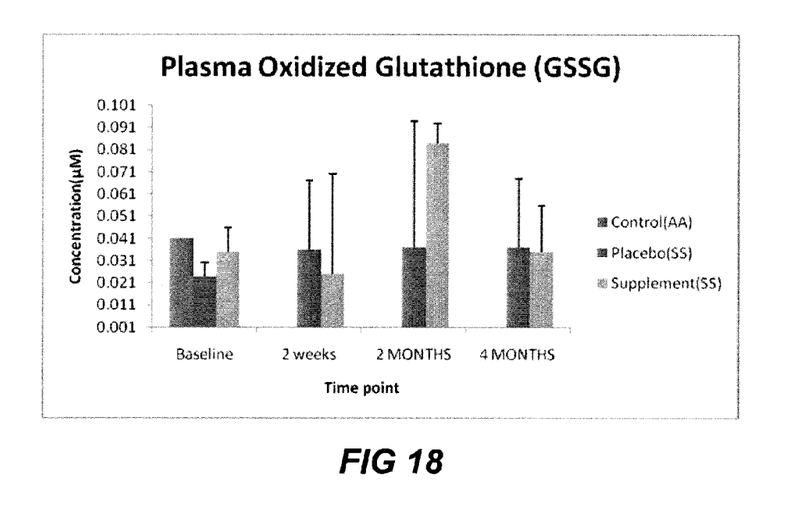
FIG. 18 is a diagram showing that the supplemented group showed an increased in the circulating levels of oxidized glutathione (GSSG) by 154% vs. no change in plasma levels for the placebo group, over 2 months. The decrease at 4 months in the supplemented group may be due to number of participants at that time.
Figure 19:
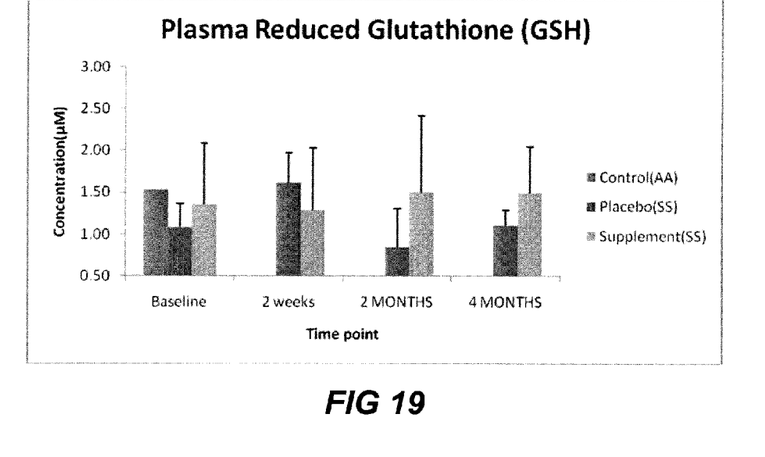
FIG. 19 is a diagram showing that glutathione levels increased by 10.4% for the supplemented group vs. a 2.8% increase for the placebo group. Glutathione is an antioxidant needed to reduce the level of hemolysis and other oxidative tissue damage seen in sickle cell anemia.

After 3-4 months of supplementation (a short time for a dietary supplementation study), there was a 34.9% increase in plasma glutamine level for the group on supplement cookie compared with a 2.9% decrease among the placebo group over the same time period (FIG. 10). Similarly the histidine and citrulline levels increased by 15.2% and 84.7% for the group on supplement compared with 17.8% and 18.6% increase respectively for the placebo group (FIGS. 11 and 12). Arginine has been shown to be deficient albeit very much needed in SCA patients. At baseline the plasma arginine level was higher for the placebo group compared with the supplement group. But by the 4 months after supplementation with the cookie, the serum arginine level for the group on supplement has increased by 42.7% compared with 6.9% for the group on placebo (FIG. 13). Also plasma levels of valine, omithine and cysteine (needed for the synthesis of glutathione) were higher in the group on supplement compared with the group on placebo at 4 months. Plasma valine levels increased by 11.2% for the supplement group, compared with a decrease of 2.2% for the placebo group (FIG. 14). Plasma omithine levels increased by 8.4% in the supplemented group compared with a decrease of 17.4% in the placebo group (FIG. 15). For plasma cysteine, despite the higher baseline levels for the supplement group, by four months, there was a 151.9% increase for the group on supplement compared with a 43.8% decrease for the group on placebo (FIG. 16). Similarly, the plasma level of cystine rose by 26.0% for the group on supplement compared with 7.8% for the group on placebo (FIG. 17). The plasma levels of oxidized glutathione (GSSG) were unchanged for the group on supplement compared with a 54.2% rise for the group on placebo, the latter indicating a higher level of oxidative stress than the supplemented group (FIG. 18). The reverse is true for reduced glutathione (GSH) level, which increased from baseline by 10.3% for the group on supplement, compared with a 2.8% decrease for the placebo group (FIG. 19). This is also an indication of less effective diffusion of reactive oxidant molecules over time by the placebo group compared with the supplement group, previously demonstrated by FIG. 9.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following embodiments. The embodiments are intended to cover the mentioned components and steps in any sequence which is effective to meet the objectives there intended, unless the context specifically indicates the contrary.

What is claimed is:

1. A method for providing nutritional support to a subject having sickle cell anemia, comprising:
   orally administering to a subject in need of such treatment a daily nutritional supplement having total calories of about 700-980 kcal, wherein about 10-20% of the total calories are derived from protein, about 25-40% of the total calories are derived from fat, and about 45-65% of the total calories are derived from carbohydrate.

2. The method of claim 1, wherein the nutritional supplement is administered orally in the form of a snack.

3. The method of claim 2, wherein the nutritional supplement is administered orally as the last snack before sleeping.

4. The method of claim 2, wherein the nutritional supplement is administered as snacks after each meal, 5. The method of claim 1, wherein the nutritional supplement comprises:
   protein in an amount that provides about 14% of the total calories;
   fat in an amount that provides about 32% of the total calories; and
   carbohydrate that provides about 54% of the total calories.

6. The method of claim 1, wherein the nutritional supplement comprises about 24-34 grams of protein; about 25-35 grams of fat; and about 96-135 grams of carbohydrate.

7. The method of claim 1, wherein the nutritional supplement further comprises at least one food grade amino acid selected from the group consisting of arginine, histidine, leucine, valine, cysteine and glutamine.

8. The method of claim 7, wherein the nutritional supplement comprises arginine, histidine, leucine, valine, cysteine and glutamine, and wherein each amino acid is provided at a per diem dose range of 8-14 mg/kg body weight/day.

9. The method of claim 7, wherein the nutritional supplement comprises arginine, histidine, leucine, valine, cysteine and glutamine, and wherein each amino acid is provided at a per diem dose range of 22-44 mg/kg body weight/day.

10. The method of claim 7, wherein the nutritional supplement further comprises S-allyl cysteine, S-allylmercapto cysteine and fructosyl arginine.

11. The method of claim 7, wherein the nutritional supplement further comprises a garlic extract.

12. The method of claim 1, wherein the nutritional supplement further comprises one or more antioxidants.

13. The method of claim 12, wherein the one or more antioxidants is selected from the group consisting of Vitamin A, Vitamin C, Vitamin E, β-carotene and selenium.

14. The method of claim 12, wherein the one or more antioxidants comprise Vitamin C and Vitamin E.

15. The method of claim 1, further comprising administering one or more nutrients selected from the group consisting of: Vitamin A 8,250-250,000 IU, Vitamin B-1 25-1000 mg, Vitamin B-2 25-1000 mg, Vitamin B-6 25-1000 mg, Vitamin B-12 25-1000 mcg, Vitamin C 25-1000 mg, Vitamin D 100-4000 IU, Vitamin E 25-1000 IU, Niacinamide 25-1000 mg, Para-aminobenzoic acid (PABA) 25-1000 mg, Pantothenic Acid 25-1000 mg, Choline Bitartrate 25-1000 mg, Inositol 25-1000 mg, Rutin 8.25-250 mg, Citrus Bioflavonoid Complex 8.25-250 mg, Betaine Hydrochloride 8.25-250 mg, Hesperidin Complex 1.25-50 mg, Folic Acid 100-4000 mcg, Biotin 25-1000 mcg, Calcium 10-400 mg, Iron 8.25-250 mg, Magnesium 5-100 mg, Zinc 5-100 mg, Potassium 3.75-150 mg, Manganese 1.5-60 mg, Iodine 37.5-1500 mcg, Chromium 3.75-150 mcg, and Selenium 2.5-100 mcg.

16. The method of claim 15, further comprising administering one or more compound(s) selected from the group consisting of L-lysine-L-phenylalanine, L-lysine-L-tyrosine, L-histidine-L-lysine-L-tyrosine-L-histidine, and salts thereof at a dose range of 10-150 mg/kg/day.

17. The method of claim 15, further comprising administering L-lysine-L-phenylalanine or a salt thereof at a dose range of 20-80 mg/kg/day.

18. The method of claim 1, further comprising administering a thiocyanate in an amount of 100-500 mg.

19. The method of claim 18, wherein the thiocyanate is mixed with Vitamin B6 at a weight ratio of about 20:1.

20. The method of claim 1, wherein the nutritional supplement is administered in the form of a cookie.

21. A method for reducing the resting energy expenditure to free fat mass ratio in a subject having sickle cell anemia, comprising:
    orally administering to a subject in need of such treatment a daily nutritional supplement having total calories of about 700-980 kcal, wherein about 10-20% of the total calories are derived from protein, about 25-40% of the total calories are derived from fat, and about 45-65% of the total calories are derived from carbohydrate.

22. A method for increasing the plasma amino acid level of at least one amino acid in a subject having sickle cell anemia, wherein the at least one amino acid is selected from the group consisting of glutamine, histidine, citrulline, arginine, valine, ornithine and cysteine,
    the method comprising:
    orally administering to a subject in need of such treatment a daily nutritional supplement having total calories of about 700-980 kcal, wherein about 10-20% of the total calories are derived from protein, about 25-40% of the total calories are derived from fat, and about 45-65% of the total calories are derived from carbohydrate.

23. the method of claim 1, wherein the plasma level of reduced glutathione is increased relative to the plasma level of oxidized glutathione as a result of said nutritional support.

* * * * *